United States Patent [19]
Lee et al.

[11] Patent Number: 5,952,540
[45] Date of Patent: Sep. 14, 1999

[54] PROCESS FOR PREPARING HYDROCARBONS

[75] Inventors: Kyu Wan Lee; Myoung Jae Choi; Ki Won Jun; Pyoung Ho Choi, all of Daejeon; Soo Jae Lee, Kyungsangnam-do, all of Rep. of Korea

[73] Assignee: Korea Research Institute of Chemical Technology, Daejeon, Rep. of Korea

[21] Appl. No.: 09/000,443

[22] PCT Filed: Oct. 27, 1995

[86] PCT No.: PCT/KR95/00139

§ 371 Date: Jan. 26, 1998

§ 102(e) Date: Jan. 26, 1998

[87] PCT Pub. No.: WO97/05088

PCT Pub. Date: Feb. 13, 1997

[30] Foreign Application Priority Data

Jul. 31, 1995 [KR] Rep. of Korea ................ 95-23318

[51] Int. Cl.⁶ .................... C07C 1/00; C07C 27/00; B01J 23/38
[52] U.S. Cl. .................. 585/733; 585/638; 518/700; 518/717; 518/719; 518/721; 502/330; 502/336
[58] Field of Search ................ 585/733, 638; 518/700, 717, 719, 721; 502/330, 336

[56] References Cited

U.S. PATENT DOCUMENTS 3,842,113  10/1974  Ichikawa et al. .............. 260/449 R
5,140,049  8/1992   Fiato et al. ...................... 518/700

FOREIGN PATENT DOCUMENTS 31 03 207   12/1981  Germany .
1-190638     7/1989  Japan .
4-120191     4/1992  Japan .
709645       6/1954  United Kingdom .

OTHER PUBLICATIONS

Lee et al.; Hydrogenation of Carbon Dioxide on Unpromoted and Potassium–Promoted Iron Catalysts Bull. Chem. Soc. Jpn., vol. 62, No. 8, 1989, pp. 2756–2758.

Weatherbee et al.; "Hydrogenation of $CO_2$ on Group VIII Metals—IV. Specific Activities and Selectivities of Silica–Supported Co, Fe, and Ru" Journal of Catalysis 87, 1984, pp. 352–362.

Dwyer et al.; "Hydrogenation of CO and $CO_2$ over Iron Foils—Correlations of Rate, Product Distribution and Surface Compositions" Journal of Catalysis 52, 1978, pp. 291–301.

*Primary Examiner*—Glenn Caldarola
*Assistant Examiner*—In Suk Bullock
*Attorney, Agent, or Firm*—Finnegan, Henderson, Farabow, Garrett & Dunner

[57] ABSTRACT

This invention relates to a process for preparing hydrocarbons, in particular hydrogenation of carbon dioxide over Fe-K/$Al_2O_3$ catalyst, which is reduced in hydrogen and activated in the mixture of carbon dioxide and hydrogen.

6 Claims, No Drawings

PROCESS FOR PREPARING HYDROCARBONS

BACKGROUND OF THE INVENTION

1. Field of the Invention

This invention relates to a process for preparing hydrocarbons, in particular, to a process for preparing hydrocarbons by hydrogenation of carbon dioxide over Fe-K/$Al_2O_3$ catalyst, which is reduced under hydrogen atmosphere after activated in mixture of carbon dioxide and hydrogen.

2. Description of Related Art

Carbon dioxide is the so called 'greenhouse gas'. Accumulation of carbon dioxide in the atmosphere caused by a huge amount of the fossil fuel consumption is now regarded as one of the major reasons for Global Warming.

To conserve the environment, it will be necessary to restrict the use of fossil fuel. However, it is expected that it will be necessary to use fuel and materials containing carbon atom continuously. A possible contribution to reducing carbon dioxide accumulation would be the chemical transformation of carbon dioxide into valuable compounds or fuel using suitable catalysts. This would provide a means of recycling carbon dioxide exhausted from combustion of fuel.

The material manufactured from the reduction of carbon dioxide should be consumed in a wide scope because carbon dioxide is exhauted in enormous volume. Therefore, the effective conversion of carbon dioxide to hydrocarbons would be regarded as one of the most promising routes for carbon dioxide fixation by catalytic process.

Processes for preparing hydrocarbons by hydrogenation of carbon monoxide have been studied widely and applied in commercial quantity. Catalysts and technology used for the hydrogenation of carbon monoxide also can be applied to hydrogenation of carbon dioxide. But chemical properties of carbon monoxide and carbon dioxide are quite different from each other, so the yield of hydrocarbons, especially hydrocarbons having 2 or more carbon atoms (hereinafter called "$C_{2+}$ hydrocarbons") is extremely low.

It requires emergently new catalyst for preparing hydrocarbons in high yield without forming of by-product such as carbon monoxide.

$CO_2 \rightarrow$ Hydrocarbons

There are two general methods for preparing $C_{2+}$ hydrocarbons using carbon dioxide. The first method is comprised of two-step reactions, that is, conversion of carbon dioxide to methanol and continuous conversion of the methanol to hydrocarbons. The second method is reacting carbon dioxide with hydrogen to obtain hydrocarbons directly.

Conventional methods for preparing $C_{2+}$ hydrocarbons using carbon dioxide according to the above first method are as follows.

Japanese patent application No. 89-190,638 discloses a method in which carbon dioxide is reduced at 300° C., 10 atm over catalysts in a fixed bed reactor. The catalysts used in the above reduction are composed of $CuO$—$ZnO$—$Al_2O_3$ and dealuminated H—Y Zeolite of $SiO_2/Al_2O_3$ molar ratio $\leq 10$. As the result of reduction, the yield of hydrocarbon was 9.7% and the conversion of carbon dioxide was 20.3%.

Japanese patent application No. 92-120,191 discloses a method in which preparing of methanol from carbon dioxide, and $C_{2+}$ hydrocarbons from methanol are performed in two reactors. Carbon dioxide is converted to methanol in the first reactor, and a mixture containing methanol is converted to $C_{2+}$ hydrocarbons in second reactor.

$CO_2 + 3H_2 \rightarrow CH_3OH + H_2O$ $CH_3OH \rightarrow$ Hydrocarbons

The above two reactions are performed under different reaction conditions such as catalyst, temperature, pressure, etc. due to the difference of their optimum conditions at each reaction. The first reaction is performed appropriately at 250° C., 80 atm, 4700 $h^{-1}$ of the space velocity over $CuO$—$ZnO$—$Cr_2O_3$—$Al_2O_3$ catalyst. On the other hand the second reaction is performed appropriately at 300° C., 1 atm, 1680 $h^{-1}$ of the space velocity. As the result of the first reaction, the conversion of hydrocarbon was 32.1%, the selectivities to methanol and carbon monoxide were 24.9% and 7.2% respectively. The mixture passed through the first reactor was introduced into the second reactor. In the second reactor the conversion of carbon dioxide to hydrocarbon was not seen, but 32.1% of the methanol formed in the first reactor was converted to hydrocarbons.

According to the results of conventional studies, when $C_{2+}$ hydrocarbons was prepared from carbon dioxide, the conversion of carbon dioxide was less than 35% and the yield of hydrocarbon was less than 30%.

G. A. Somoijai et al. reported that carbon dioxide was reduced by hydrogen at 300° C., 6 atm over iron based catalyst to form hydrocarbons as desired products. As the result, 97% of hydrocarbons are methane and $C_{2+}$ hydrocarbons formation is very low [J. Catal., 52,291(1978)].

Also C. H. Bartholomew et al. reported that carbon dioxide was reduced at 450~630 K, 1~11 atm in the molar feed ratio of $H_2/CO_2 = 4$ over catalysts. The catalysts were prepared by impregnation of silica with transition metal such as Co, Fe, Ru, etc. in 15% to weight of carrier used. As the result, methane was formed as major, $C_{2+}$ hydrocarbons were less than 10% of hydrocarbons and the conversion of carbon dioxide was less than 15% [J. Catal.87, 352(1984)].

Also M. D. Lee et al. reported that carbon dioxide was reduced at 320° C., 10 atm, 600 ml/g/h of the space velocity and $H_2/CO_2 = 4$ over K-Fe(K=3 atom %) catalyst. As the result, the conversion of carbon dioxide was 35% and the yields of hydrocarbons and $C_{2+}$ hydrocarbons s were 28% and 23%, respectively[Bull. Chem. Soc. Jpn, 62, 2756 (1989)].

The inventors of this invention have investigated a new method for preparing hydrocarbons, especially $C_{2+}$ hydrocarbons by hydrogenation of carbon dioxide. As the result, this invention is completed by following method; Fe-K/$Al_2O_3$ catalyst was reduced with hydrogen and activated with the mixture of carbon dioxide and hydrogen, and then hydrogen and carbon dioxide ($H_2/CO_2 = 1.0 \sim 5.0$) were introduced to contact with the pretreated catalyst at 200~500° C., 1~100 atm, 500~20,000 $h^{-1}$ of the space velocity.

In the process according to this invention, the conversion of carbon dioxide was raised much more than 50%, the yields of hydrocarbons and $C_{2+}$ hydrocarbons are more than 50% and 45% respectively, and carbon monoxide generation is minimized.

SUMMARY OF THE INVENTION

The object of this invention is to provide a new process for preparing hydrocarbons which are valuable in chemical industry.

The other object of this invention is to provide a new process for reducing the emission of carbon dioxide into the atmosphere.

This invention relates to a process for preparing hydrocarbon by hydrogenation of carbon dioxide over catalyst, wherein said catalyst is pretreated Fe-K/$Al_2O_3$ with reduction and activation.

DETAILED DESCRIPTION OF THE INVENTION

This invention relates to a method for preparing hydrocarbons by reducing and activating of Fe-K/$Al_2O_3$ catalyst, and reacting carbon dioxide with hydrogen under said catalyst.

Catalyst used in this invention is iron and potassium supported on alumina carrier, and a process for preparing the catalyst is as follows:

Solution of iron-containing salts such as iron chloride, iron nitrate, iron sulfate, iron acetate, iron oxalate etc. or potassium-containing salts such as potassium chloride, potassium carbonate, potassium nitrate, potassium acetate etc. is impregnated into alumina and mixed. Then it is dried at 80~200° C. for 5~48 hours, and calcinated at 400~700° C. for 5~48 hours. A catalyst obtained by the above method becomes mixed with iron oxide, potassium oxide and aluminum oxide. Preferably 5~50 wt % of iron to a whole catalyst is supported, 0.1~1.5 atomic ratio of potassium to iron is mixed and $\gamma$-$Al_2O_3$ is used.

In previous methods, potassium has been used as mixing with iron-based catalyst, but the atomic ratio of potassium to iron wasn't more than 0.05. According to this invention if the ratio of potassium to iron is less than 0.1, it isn't proper to activate acidic carbon dioxide because basicity of a catalyst doesn't sufficiently increase. If the atomic ratio of potassium to iron is more than 1.5, the activity of catalyst is poor because total contents of iron as activating component is decreased greatly.

In this invention, $\gamma$—$Al_2O_3$ not only plays a role of carrier but also increases activity and selectivity of the catalyst through interaction with iron. In the case of using silica which only plays a role of carrier, activity and selectivity of iron-based catalyst are not increased. If the content of supported iron is less than 5 wt %, activity of catalyst is decreased and if it is more than 50 wt %, advantages due to interaction with aluminum oxide cannot be gained.

According to this invention to obtain effective catalyst, Fe-K/$Al_2O_3$ catalyst must be pretreated by process which is consisted of reduction and activation of the catalyst. Reduction is performed by flowing hydrogen into the catalyst at 1~10 atm, 300~500° C., 20~100 ml/g-cat./min of the flow rate, and iron oxide reduced changes to iron metal. Activation is performed by flowing mixture of hydrogen and carbon dioxide into Fe-K/$Al_2O_3$ at 200~400° C., 10~40 atm, 2~200 ml/g-cat./min of the flow rate, and flowing carrier gas selected from the group which is consisted of nitrogen, argon and helium into Fe-K/$Al_2O_3$ at 100~400° C., 1~10 atm, 10~100 ml/g-cat./min. Iron of the activated Fe-K/$Al_2O_3$ catalyst exists in a carburized state appropriately, and this effectively acts on activating of carbon dioxide.

The reactor for preparing hydrocarbons using carbon dioxide can be fixed bed reactor, fluidized bed reactor or slurry type reactor of liquid phase. The hydrogenation of carbon dioxide is performed under mixture gas ($H_2$/$CO_2$= 1.0~5.0 v/v) at 200~500° C., 1~100 atm, 500~20,000 $h^{-1}$ of the space velocity. Stoichiometric ratio of the mixture gas ($H_2$/$CO_2$) is 3~4 v/v. If the condition of hydrogenation is out of this range, the conversion of carbon dioxide goes down. If the ratio of mixture gas is less than 1.0 v/v or more than 5.0 v/v, the conversion of carbon dioxide become too low. If reaction temperature is lower than 200° C., the conversion goes down, and if it is higher than 500° C., the selectivity to $C_{2+}$ hydrocarbons become low because the more reaction temperature is increased, the more formation of methane is increased. If reaction pressure is less than 1 atm, reaction rate is too slow and if it is more than 100 atm, the control of reactions conditions controlling is difficult. If the space velocity is less than 500 $h^{-1}$, the selectivity is too low and if it is more than 20,000 $h^{-1}$, the conversion is low because the contact time between reactant and catalyst is too short.

According to the above description the process for preparing hydrocarbons is consisted of pretreatment of Fe-K/$Al_2O_3$ catalyst through reduction by hydrogen and activation by carbon dioxide and hydrogen, and the hydrogenation of carbon dioxide over Fe-K/$Al_2O_3$ catalyst pretreated.

Accordingly, this invention is useful to the preparation of $C_{2+}$ hydrocarbons from carbon dioxide because the conversion of carbon dioxide is high and the selectivity to $C_{2+}$ hydrocarbons is very high.

This invention may be illustrated in more detail by the following examples but it is not limited by the examples.

EXAMPLE 1

In 15 g of Fe($NO_3$)$_3$·9$H_2O$ and 1.3 g of $K_2CO_3$ in 100 g of water 10 g of $\gamma$—$Al_2O_3$ was added and vigorously stirred to evaporate water. After the evaporation of water, the reaction mixture was dried at 120° C. for 24 hours and calcinated at 500° C. for 12 hours.

To reduce the catalyst hydrogen was flowed into 0.5 g of calcination-completed Fe-K/$Al_2O_3$ catalyst at 450° C., 60 ml/g-cat./min for 24 hours in a flow-type reactor. To activate the catalyst carbon dioxide and hydrogen($H_2$/$CO_2$=3 v/v) were flowed into Fe-K/$Al_2O_3$ catalyst at 10 atm, 300° C., 32 ml/g-cat./min for 16 hours, and then nitrogen was flowed into Fe-K/$Al_2O_3$ catalyst at 200° C., 1 atm, 20 ml/g-cat./min for 1 hour.

To prepare hydrocarbons a mixture of carbon dioxide and hydrogen($H_2$/$CO_2$=3 v/v) was passed through the pretreated Fe-K/$Al_2O_3$ catalyst at 300° C., 10 atm, 1330 $h^{-1}$ space velocity.

The results are given in the following Table 1.

EXAMPLE 2

A mixture of carbon dioxide and hydrogen($H_2$/$CO_2$=3 v/v) was passed through the Fe-K/$Al_2O_3$ catalyst pretreated by the above Example 1 at 300° C., 20 atm, 1330 $h^{-1}$ space velocity to prepare hydrocarbons.

The results are given in the following Table 1.

EXAMPLE 3

A mixture of carbon dioxide and hydrogen($H_2$/$CO_2$=3 v/v) was passed through the Fe-K/$Al_2O_3$ catalyst pretreated by the above Example 1 at 400° C., 20 atm, 1330 $h^{-1}$ space velocity to prepare hydrocarbons.

The results are given in the following Table 1.

EXAMPLE 4

In 15 g of Fe($NO_3$)$_3$·9$H_2O$ and 0.51 g of $K_2CO_3$ in 100 g of water 10 g of $\gamma$—$Al_2O_3$ was added and vigorously stirred to evaporate water. After the evaporation of water, the reaction mixture was dried at 120° C. for 24 hours and calcinated at 500° C. for 12 hours.

To reduce the catalyst hydrogen was flowed into 0.5 g of calcination-completed Fe-K/$Al_2O_3$ catalyst at 400° C., 60 ml/g-cat./min for 24 hours in a flow-type reactor. To activate the of catalyst carbon dioxide and hydrogen($H_2$/$CO_2$=3 v/v) were flowed into Fe-K/$Al_2O_3$ catalyst at 20 atm, 300° C., 32 ml/g-cat./min for 16 hours, and then nitrogen was flowed into Fe-K/$Al_2O_3$ catalyst at 300° C., 1 atm, 20 ml/g-cat./min for 1 hour.

To prepare hydrocarbons a mixture of carbon dioxide and hydrogen($H_2/CO_2$=3 v/v) was passed through the pretreated Fe-K/$Al_2O_3$ catalyst at 400° C., 20 atm, 1330 $h^{-1}$ space velocity.

The results are given in the following Table 1.

EXAMPLE 5

In 15 g of Fe(NO$_3$)$_3$·9H$_2$O and 2.6 g of K$_2$CO$_3$ in 100 g of water 10 g of γ—Al$_2$O$_3$ was added and vigorously stirred to evaporate water. After the evaporation of water, the reaction mixture was dried at 120° C. for 24 hours and calcinated at 500° C. for 12 hours.

To reduce the catalyst, hydrogen was flowed into 0.5 g of calcination-completed Fe-K/Al$_2$O$_3$ catalyst at 450° C., 60 ml/g-cat./min for 24 hours in a flow-type reactor. To activate the catalyst carbon dioxide and hydrogen($H_2/CO_2$=3 v/v) were flowed into Fe-K/Al$_2$O$_3$ catalyst at 20 atm, 350° C., 32 ml/g-cat./min for 16 hours, and then nitrogen was flowed into Fe-K/Al$_2$O$_3$ catalyst at 300° C., 1 atm, 20 ml/g-cat./min for 1 hour.

To prepare hydrocarbons mixture gas of carbon dioxide and hydrogen($H_2/CO_2$=3 v/v) was passed through the pretreated Fe-K/Al$_2$O$_3$ catalyst at 350° C., 20 atm, 1330 $h^{-1}$ space velocity.

The results are given in the following Table 1.

EXAMPLE 6

In 15 g of Fe(NO$_3$)$_3$·9H$_2$O and 2.6 g of K$_2$CO$_3$ in 100 g of water,10 g of γ—Al$_2$O$_3$ was added and vigorously stirred to evaporate water. After the evaporation of water, the reaction mixture was dried at 120° C. for 24 hours and calcinated at 500° C. for 12 hours.

To reduce the catalyst, hydrogen was flowed into 0.5 g of calcination-completed Fe-K/Al$_2$O$_3$ catalyst at 450° C., 80 ml/g-cat./min for 24 hours in a flow-type reactor. To activate catalyst, carbon dioxide and hydrogen($H_2/CO_2$=3 v/v) was flowed into Fe-K/Al$_2$O$_3$ catalyst at 30 atm, 300° C., 32 ml/g-cat./min for 16 hours, and then nitrogen was flowed into Fe-K/Al$_2$O$_3$ catalyst at 300° C., 1 atm, 40 ml/g-cat./min for 2 hours.

To prepare hydrocarbons a mixture of carbon dioxide and hydrogen($H_2/CO_2$=3 v/v) was passed through the pretreated Fe-K/Al$_2$O$_3$ catalyst at 300° C., 30 atm, 1330 $h^{-1}$ space velocity.

The results are given in the following Table 1.

COMPARATIVE EXAMPLE 1

Hydrocarbons were prepared by the same manner with the above Example 1 except Fe-K/silica catalyst was used instead of Fe-K/Al$_2$O$_3$ catalyst.

The results are given in the following Table 1.

COMPARATIVE EXAMPLE 2

Hydrocarbons were prepared by the same manner with the above Example 1 except Fe-K/silica catalyst was used instead of Fe-K/Al$_2$O$_3$ catalyst and K$_2$CO$_3$ wasn't added.

The results are given in the following Table 1.

COMPARATIVE EXAMPLE 3

Hydrocarbons were prepared by the same manner with the above Example 1 except activation of catalyst was not performed.

The results are given in the following Table 1.

COMPARATIVE EXAMPLE 4

Hydrocarbons were prepared by the same manner with the above Example 4 except for using 0.13 g of K$_2$CO$_3$.

The results are given in the following Table 1.

COMPARATIVE EXAMPLE 5

Hydrocarbons were prepared by the same manner with the above Example 1 except for using catalyst prepared as follows:

Ammonium hydroxide was slowly added in 15 g of Fe(NO$_3$)$_3$·9H$_2$O in 100 g of water to be pH 8.5 and to form precipitates. Then the precipitates were dried at 120° C. for 24 hours and calcinated at 500° C. for 12 hours. This was mixed with 1.3 g of potassium carbonate solution in 100 g of water and vigorously stirred, and water was evaporated by heating. After the evaporation of water, it was dried at 120° C. for 12 hours and calcinated at 500° C. for 3 hours.

The results are given in the following Table 1.

TABLE 1

| Example | Conversion rate (%) | Yield (C %) hydrocarbons | $C_1$* | $C_{2+}$** |
|---|---|---|---|---|
| Example 1 | 57.7 | 50.4 | 3.6 | 46.8 |
| Example 2 | 56.0 | 54.7 | 4.3 | 50.4 |
| Example 3 | 69.6 | 66.9 | 10.7 | 56.2 |
| Example 4 | 67.3 | 63.3 | 11.5 | 51.8 |
| Example 5 | 70.4 | 68.6 | 7.8 | 60.8 |
| Example 6 | 61.8 | 60.1 | 3.3 | 56.8 |
| Comp. Example 1 | 14.7 | 5.3 | 0.7 | 4.6 |
| Comp. Example 2 | 22.1 | 8.5 | 5.1 | 3.4 |
| Comp. Example 3 | 31.8 | 25.6 | 3.5 | 22.1 |
| Comp. Example 4 | 49.7 | 45.7 | 20.7 | 25.0 |
| Comp. Example 5 | 27.7 | 21.0 | 2.3 | 18.7 |

$C_1$*: methane
$C_{2+}$**: hydrocarbons having 2 or more carbon atoms

What is claimed is:

1. A process for preparing hydrocarbons by hydrogenation of carbon dioxide over a catalyst, wherein said catalyst is Fe-K/γ—Al$_2$O$_3$ having a 0.1~1.5 atomic ratio of K/Fe and including 5~50 wt % of Fe to total catalyst weight and wherein prior to said hydrogenation said catalyst is reduced under hydrogen gas and activated under a mixture of hydrogen and carbon dioxide.

2. The process according to claim 1, wherein said reduction is performed by flowing hydrogen on the Fe-K/γ—Al$_2$O$_3$ at 300~500° C., 1~10 atm, 20~100 ml/g-cat./min of the flow rate.

3. The process according to claim 1, wherein said activation is performed by flowing the mixture of hydrogen and carbon dioxide on Fe-K/γ—Al$_2$O$_3$ at 200~400° C., 10~40 atm, 2~200 ml/g-cat./min of the flow rate, and flowing a gas selected from the group consisting of nitrogen, argon and helium on Fe-K/γ-Al$_2$O$_3$ at 100~400° C., 1~10 atm, 10~100 ml/g-cat./min.

4. The process according to claim 1, wherein said hydrogenation is preformed by flowing mixture gas ($H_2/CO_2$=1.0~5.0 v/v) into the reactor at 200~500° C., 1~100 atm, 500~20,000 $h^{-1}$ of the space velocity.

5. The process according to claim 4, wherein said mixture gas contains one or more selected from the group which is consisted of nitrogen, argon and helium.

6. The process according to claim 4, wherein said reactor is a fixed bed reactor, a fluidized bed reactor or slurry type reactor.

* * * * *